(12) United States Patent
Hodge et al.

(10) Patent No.: US 7,514,555 B2
(45) Date of Patent: Apr. 7, 2009

(54) COMPOUNDS FOR THE TREATMENT OF METABOLIC DISORDERS

(75) Inventors: Kirvin L. Hodge, Laurel, MD (US); Shalini Sharma, Gaithersburg, MD (US); Reid W. von Borstel, Potomac, MD (US); Stephen D. Wolpe, Boyds, MD (US)

(73) Assignee: Wellstat Therapeutics Corporation, Gaithersburg, MD (US)

( * ) Notice: Subject to any disclaimer, the term of this patent is extended or adjusted under 35 U.S.C. 154(b) by 82 days.

(21) Appl. No.: 10/531,618

(22) PCT Filed: Apr. 8, 2004

(86) PCT No.: PCT/US2004/010799

§ 371 (c)(1),
(2), (4) Date: Apr. 14, 2005

(87) PCT Pub. No.: WO2004/091486

PCT Pub. Date: Oct. 28, 2004

(65) Prior Publication Data

US 2006/0014784 A1    Jan. 19, 2006

Related U.S. Application Data

(60) Provisional application No. 60/462,960, filed on Apr. 15, 2003.

(51) Int. Cl.
 C07D 213/00 (2006.01)
 C07D 211/70 (2006.01)
 C07C 69/76 (2006.01)
 C07C 229/00 (2006.01)
 A61K 31/47 (2006.01)

(52) U.S. Cl. ............... 546/1; 546/329; 560/8; 560/19; 560/39; 560/75; 514/310; 514/866

(58) Field of Classification Search ........... 514/310
See application file for complete search history.

(56) References Cited

U.S. PATENT DOCUMENTS

| | | | | |
|---|---|---|---|---|
| 5,219,579 | A * | 6/1993 | Tisdale et al. | 424/573 |
| 5,604,225 | A * | 2/1997 | Reiffen et al. | 514/230.8 |
| 5,665,387 | A * | 9/1997 | Mathieu et al. | 424/464 |
| 6,143,787 | A | 11/2000 | Moinet et al. | |
| 6,156,781 | A * | 12/2000 | Talley et al. | 514/406 |
| 6,307,080 | B1 * | 10/2001 | Pischel et al. | 556/131 |
| 6,858,602 | B2 | 2/2005 | Sharma et al. | |
| 6,916,848 | B2 | 7/2005 | Sharma | |
| 6,924,314 | B2 | 8/2005 | Sharma et al. | |
| 6,946,491 | B2 | 9/2005 | Sharma et al. | |
| 7,012,071 | B2 | 3/2006 | Sharma et al. | |
| 7,041,659 | B2 | 5/2006 | Sharma | |
| 7,045,541 | B2 | 5/2006 | Sharma et al. | |
| 7,101,910 | B2 | 9/2006 | Sharma | |
| 2002/0028943 | A1 * | 3/2002 | Griffin | 546/223 |
| 2003/0149107 | A1 | 8/2003 | Sharma et al. | |
| 2005/0090555 | A1 | 4/2005 | Sharma et al. | |
| 2005/0256333 | A1 | 11/2005 | Sharma et al. | |

FOREIGN PATENT DOCUMENTS

| | | |
|---|---|---|
| WO | WO02/100341 | 12/2002 |
| WO | 2004/041165 A2 | 5/2004 |
| WO | 2006/127133 A2 | 5/2004 |
| WO | WO2004/073611 | 9/2004 |

OTHER PUBLICATIONS

Younis, et al., "The prevention of type 2 diabetes mellitus: recent advances", QJ Med., vol. 97, pp. 451-455, 2004.
Goff, et al., "Prevention of Cardiovascular Disease in Persons with type 2 diabetes Mellitus: Current Knowledge and Rational for the Action to Control Cardiovascular Risk in Diabetes (ACCORD) Trial", AM J Cardiol., 99(12A): S4-S20, 2007. (Abstract).
Knowler, et al., "Perspectives in Diabetes: Preventing Non-Insulin-Dependent Diabetes", Diabetes, vol. 44, pp. 483-488, 1995.
Friedman, et al., "Impaired Glucose Transport and Insulin Receptor Tyrosine Phosphorylation in Skeletal Muscle From Obese Women with Gestational Diabetes", Diabetes, vol. 48, pp. 1807-1814, Sep. 1999.
Kilpatrick, et al. "Insulin Resistance, the Metabolic Syndrome, and Complication Risk in Type 1 Diabetes", Diabetes Care, vol. 30, No. 3, pp. 707-712, Mar. 2007.

(Continued)

*Primary Examiner*—Kevin E Weddington
(74) *Attorney, Agent, or Firm*—Lewis J. Kreisler

(57) ABSTRACT

Agents useful for the treatment of various metabolic disorders, such as insulin resistance syndrome, diabetes, hyperlipidemia, fatty liver disease, cachexia, obesity, atherosclerosis and arteriosclerosis are disclosed. Wherein n is 1 or 2; m is 0, 1, 2, 3 or 4; q is 0 or 1; t is 0 or 1; $R^2$ is alkyl having from 1 to 3 carbon atoms; $R^3$ is hydrogen, halo, alkyl having from 1 to 3 carbon atoms, or alkoxy having from 1 to 3 carbon atoms; A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula I by a ring carbon; and $R^1$ is hydrogen or alkyl having 1 or 2 carbon atoms, provided that when m is 0 or 1, $R^1$ is not hydrogen. Alternatively, when $R^1$ is hydrogen, the biologically active agent can be a pharmaceutically acceptable salt of the compound of Formula I.

(I)

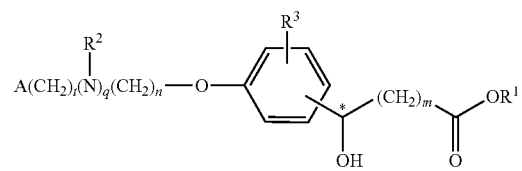

22 Claims, No Drawings

OTHER PUBLICATIONS

Pending (as of Mar. 26, 2007) claims from U.S. Appl. No. 10/566,302.

Pending (as of Mar. 26, 2007) claims from U.S. Appl. No. 10/553,936.

Pending (as of Mar. 26, 2007) claims from U.S. Appl. No. 10/554,586.

Pending (as of Mar. 26, 2007) claims from U.S. Appl. No. 11/535,779.

Child, et al., "Fenbufen, a New Anti-Inflammatory Analgesic: Synthesis and Structure-Activity Relationships of Analogs", Journal of Pharmaceutical Sciences, 1977, 66(4), pp. 466-476.

Connolly, et al., "Design and Synthesis of a Novel and Potent Series of Inhibitors of Cytosolic Phospholipase A2 Based on a 1,3-Disubstituted Propan-2-one Skeleton", Journal of Medicinal Chemistry, 2002, 45(6), pp. 1348-1362.

Flynn, et al., "One-Pot Synthesis of Benzol[b]furan and Indole Inhibitors of Tubulin Polymerization", Journal of Medicinal Chemistry, 2002, 45(12), pp. 2670-2673.

Argiles, et al., "Journey from cachexia to obesity by TNF", The FASEB Journal, 1997, 11(10), pp. 743-751. (Abstract).

de Alvaro, et al., "Tumor necrosis factor alpha produces insulin resistance in skeletal muscle by activation of inhibitor kappaB kinase in a p38 MAPK-dependent manner", J. Biol. Chem., 2004, 279(17), pp. 17070-17078. (Abstract).

Rofe, et al, "Altered insulin response to glucose in weight-losing cancer patients", Anticancer Research, 1994, 14(2B); pp. 647-650. (Abstract).

Tayek, "A review of cancer cachexia and abnormal glucose metabolism in humans with cancer", Journal of the American College of Nutrition, 1992, 11(4), pp. 445-456. (Abstract).

Wedick, et al., "Insulin resistance precedes weight loss in adults without diabetes: the Rancho Bernardo Study", American Journal of Epidemiology, 2001, 153(12), pp. 1199-1205. (Abstract).

Pending (as of Dec. 18, 2006) claims from U.S. Appl. No. 10/532,690.

\* cited by examiner

COMPOUNDS FOR THE TREATMENT OF METABOLIC DISORDERS

REFERENCE TO PRIOR APPLICATIONS

This is the national phase under 35 U.S.C. §371 of International Application No. PCT/US2004/010799, having an international filing date of Apr. 8, 2004. This application claims priority of U.S. Provisional Application No. 60/462,960, filed Apr. 15, 2003, the contents of which are hereby incorporated by reference.

BACKGROUND OF THE INVENTION

Diabetes mellitus is a major cause of morbidity and mortality. Chronically elevated blood glucose leads to debilitating complications: nephropathy, often necessitating dialysis or renal transplant; peripheral neuropathy; retinopathy leading to blindness; ulceration of the legs and feet, leading to amputation; fatty liver disease, sometimes progressing to cirrhosis; and vulnerability to coronary artery disease and myocardial infarction. There are two primary types of diabetes. Type I, or insulin-dependent diabetes mellitus (IDDM) is due to autoimmune destruction of insulin-producing beta cells in the pancreatic islets. The onset of this disease is usually in childhood or adolescence. Treatment consists primarily of multiple daily injections of insulin, combined with frequent testing of blood glucose levels to guide adjustment of insulin doses, because excess insulin can cause hypoglycemia and consequent impairment of brain and other functions.

Type II, or noninsulin-dependent diabetes mellitus (NIDDM) typically develops in adulthood. NIDDM is associated with resistance of glucose-utilizing tissues like adipose tissue, muscle, and liver, to the actions of insulin. Initially, the pancreatic islet beta cells compensate by secreting excess insulin. Eventual islet failure results in decompensation and chronic hyperglycemia. Conversely, moderate islet insufficiency can precede or coincide with peripheral insulin resistance. There are several classes of drugs that are useful for treatment of NIDDM: 1) insulin releasers, which directly stimulate insulin release, carrying the risk of hypoglycemia; 2) prandial insulin releasers, which potentiate glucose-induced insulin secretion, and must be taken before each meal; 3) biguanides, including metformin, which attenuate hepatic gluconeogenesis (which is paradoxically elevated in diabetes); 4) insulin sensitizers, for example the thiazolidinedione derivatives rosiglitazone and pioglitazone, which improve peripheral responsiveness to insulin, but which have side effects like weight gain, edema, and occasional liver toxicity; 5) insulin injections, which are often necessary in the later stages of NIDDM when the islets have failed under chronic hyperstimulation.

Insulin resistance can also occur without marked hyperglycemia, and is generally associated with atherosclerosis, obesity, hyperlipidemia, and essential hypertension. This cluster of abnormalities constitutes the "metabolic syndrome" or "insulin resistance syndrome". Insulin resistance is also associated with fatty liver, which can progress to chronic inflammation (NASH; "nonalcoholic steatohepatitis"), fibrosis, and cirrhosis. Cumulatively, insulin resistance syndromes, including but not limited to diabetes, underlie many of the major causes of morbidity and death of people over age 40.

Despite the existence of such drugs, diabetes remains a major and growing public health problem. Late stage complications of diabetes consume a large proportion of national health care resources. There is a need for new orally active therapeutic agents which effectively address the primary defects of insulin resistance and islet failure with fewer or milder side effects than existing drugs.

Currently there are no safe and effective treatments for fatty liver disease. Therefore such a treatment would be of value in treating this condition.

WO 02/100341 (Wellstat Therapeutics Corp.) discloses certain compounds substituted by hydrogen or an oxo group at the final position of the acid, for example 4-(3-(2,6-Dimethylbenzyloxy)phenyl)-butyric acid and 4-(3-(2,6-Dimethylbenzyloxy)phenyl)-4-oxobutyric acid. WO 02/100341 does not disclose any compounds within the scope of Formula I shown below, in which the final position of the acid is hydroxy-substituted.

SUMMARY OF THE INVENTION

This invention provides a biologically active agent as described below. This invention provides the use of the biologically active agent described below in the manufacture of a medicament for the treatment of insulin resistance syndrome, diabetes, cachexia, hyperlipidemia, fatty liver disease, obesity, atherosclerosis or arteriosclerosis. This invention provides methods of treating a mammalian subject with insulin resistance syndrome, diabetes, cachexia, hyperlipidemia, fatty liver disease, obesity, atherosclerosis or arteriosclerosis comprising administering to the subject an effective amount of the biologically active agent described below. This invention provides a pharmaceutical composition comprising the biologically active agent described below and a pharmaceutically acceptable carrier.

The biologically active agent in accordance with this invention is a compound of Formula I:

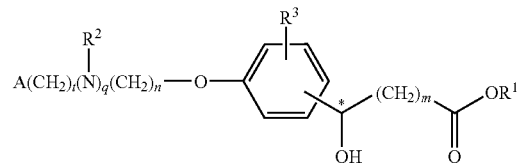

Formula I wherein n is 1 or 2; m is 0, 1, 2, 3 or 4; q is 0 or 1; t is 0 or 1; $R^2$ is alkyl having from 1 to 3 carbon atoms; $R^3$ is hydrogen, halo, alkyl having from 1 to 3 carbon atoms, or alkoxy having from 1 to 3 carbon atoms;

A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula I by a ring carbon; and $R^1$ is hydrogen or alkyl having 1 or 2 carbon atoms, provided that when m is 0 or 1, $R^1$ is not hydrogen. Alternatively, when $R^1$ is hydrogen, the biologically active agent can be a pharmaceutically acceptable salt of the compound of Formula I.

The biologically active agents described above have activity in one or more of the biological activity assays described below, which are established animal models of human diabetes and insulin resistance syndrome. Therefore such agents would be useful in the treatment of diabetes and insulin resistance syndrome. All of the exemplified compounds that were tested demonstrated activity in at least one of the biological activity assays in which they were tested.

DETAILED DESCRIPTION OF THE INVENTION

Definitions

As used herein the term "alkyl" means a linear or branched-chain alkyl group. An alkyl group identified as having a certain number of carbon atoms means any alkyl group having the specified number of carbons. For example, an alkyl having three carbon atoms can be propyl or isopropyl; and alkyl having four carbon atoms can be n-butyl, 1-methylpropyl, 2-methylpropyl or t-butyl.

As used herein the term "halo" refers to one or more of fluoro, chloro, bromo, and iodo.

As used herein the term "perfluoro" as in perfluoromethyl or perfluoromethoxy, means that the group in question has fluorine atoms in place of all of the hydrogen atoms.

As used herein "Ac" refers to the group $CH_3C(O)$—.

Certain chemical compounds are referred to herein by their chemical name or by the two-letter code shown below. Compound CR is included within the scope of Formula I shown above.

BI 4-(3-(2,6-Dimethylbenzyloxy)-phenyl)-4-oxobutanoic acid

CR 4-(3-(2,6-Dimethylbenzyloxy)-phenyl)-4(R)-hydroxybutanoic acid

As used herein the transitional term "comprising" is open-ended. A claim utilizing this term can contain elements in addition to those recited in such claim.

COMPOUNDS OF THE INVENTION

The asterisk in the depiction of Formula I above indicates a chorale center. This invention provides the racemate, the (R) enantiomer, and the (S) enantiomer, of the compounds of Formula I, all of which are active. Mixtures of these enantiomers can be separated by using HPLC, for example as described in Chirality 11:420-425 (1999).

In an embodiment of the agent, use, method or pharmaceutical composition described above, n is 1; q is 0; t is 0; $R^3$ is hydrogen; and A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy. In a more specific embodiment, A is 2,6-dimethylphenyl. Examples of such compounds include Compound CR.

In a preferred embodiment of the biologically active agent of this invention, the agent is in substantially (at least 98%) pure form.

Reaction Schemes

The biologically active agents of the present invention can be made in accordance with the following reaction schemes.

The compound of formula I where m is 2 to 4, q is 0, t is 0 or 1, and n is 1 or 2, $R^3$ is hydrogen, halo, alkoxy having from 1 to 3 carbon atoms or alkyl having from 1 to 3 carbon atoms, and $R^1$ is hydrogen or alkyl having from 1 to 2 carbon atoms, i.e. compounds of formula:

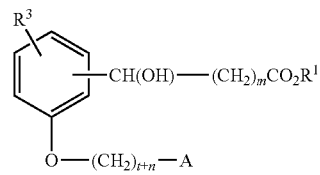

wherein A is described as above, can be prepared via reaction of scheme 1.

In the reaction scheme of Scheme 1, A, t, n, $R^3$ and $R^1$ are as above. Y is a leaving group and p is 1 to 3. The compound of formula II is converted to the compound of formula V via reaction of step (a) using Mitsunobu condensation of II with III using triphenylphosphine and diethyl azodicarboxylate or diisopropyl azodicarboxylate. The reaction is carried out in a suitable solvent for example tetrahydrofuran. Any of the conditions conventionally used in Mitsunobu reactions can be utilized to carry out the reaction of step (a).

The compound of formula V can also be prepared by etherifying or alkylating the compound of formula II with a compound of formula IV via the reaction of step (b) by using suitable base such as potassium carbonate, sodium hydride, triethylamine, pyridine and the like. In the compound of formula IV, Y, include but are not limited to mesyloxy, tosyloxy, chloro, bromo, iodo, and the like. Any conventional conditions to alkylate a hydroxyl group with a leaving group can be utilized to carry out the reaction of step (b). The reaction of step (b) is preferred over step (a) if compound of formula IV is readily available.

The compound of formula V is converted to the compound of formula VII via reaction of step (c) by alkylating the compound of formula V with the compound of formula VI. This reaction is carried out in the presence of approximately a molar equivalent of a conventional base that converts acetophenone to 3-keto ester (i.e. gamma-keto ester). In carrying out this reaction it is generally preferred but not limited to utilize alkali metal salts of hexamethyldisilane such as lithium bis-(trimethylsilyl) amide and the like. Generally this reaction is carried out in inert solvents such as tetrahydrofuran: 1,3-Dimethyl-3,4,5,6-tetrahydro-2 (1H)-pyrimidinone. Generally the reaction is carried out at temperatures of from −65° C. to 25° C. Any of the conditions conventional in such alkylation reactions can be utilized to carry out the reaction of step (c).

The compound of formula VII is converted to the compound of VIII via reaction of step (d) by reducing the ketone group to an alcohol group. The reaction is carried out by utilizing a conventional reducing agent that converts ketone to alcohol. In carrying out this reaction it is generally preferred but not limited to utilize sodium borohydride as the reducing agent. Generally this reaction is carried out in solvents such as methanol, ethanol and the like. Generally the reaction is carried out at temperatures of from 0° C. to 25° C. The product can be isolated and purified by techniques such as extraction, evaporation, chromatography, and recrystallization. Racemic mixtures of formula VIII can be separated by using HPLC. (Chirality 11:420-425 (1999).

The compound of formula VIII is the compound of formula I where $R^1$ is an alkyl group having from 1 to 2 carbon atoms.

The compound of formula VIII can be converted to the compound of formula I where $R^1$ is H by ester hydrolysis. Any conventional method of ester hydrolysis will produce the compound of formula I where $R^1$ is H.

Reaction Scheme 1

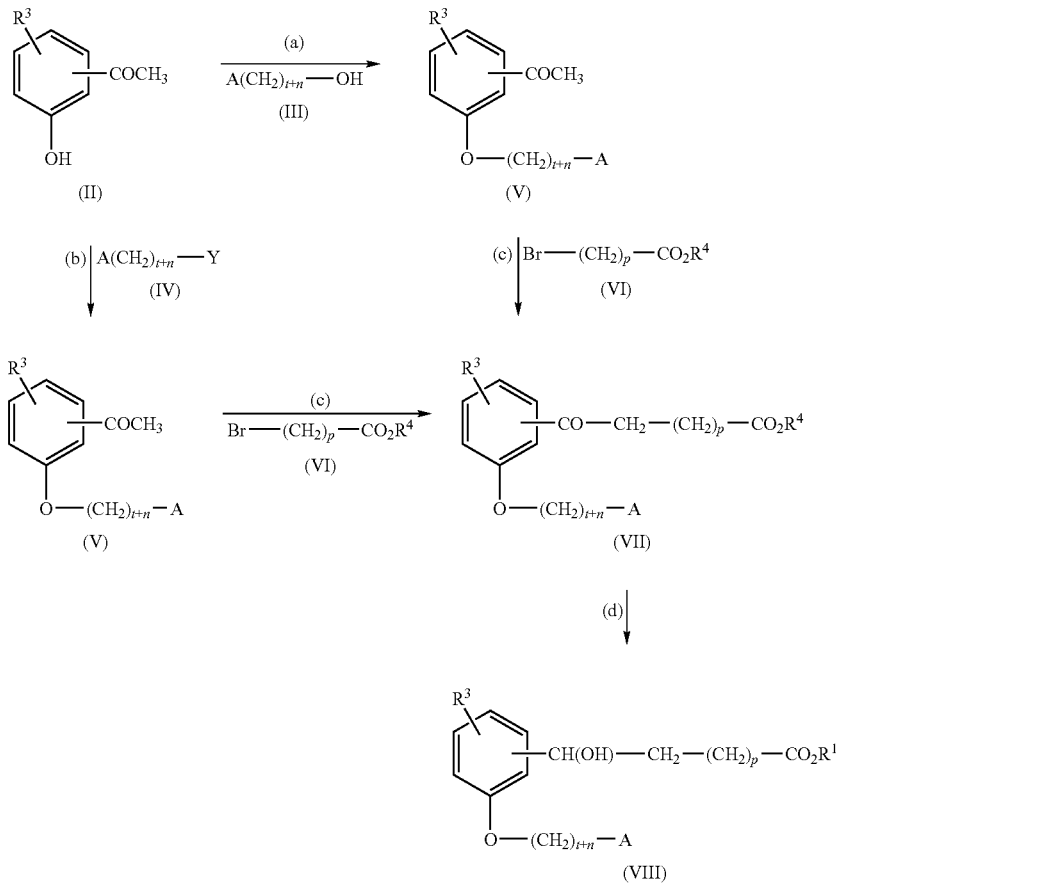

The compound of formula I where m is 2 to 4, q is 1, t is 0 or 1, and n is 1 or 2, $R^3$ is hydrogen, halo, alkoxy having from 1 to 3 carbon atoms or alkyl having from 1 to 3 carbon atoms, $R^2$ is alkyl having from 1 to 3 carbon atoms and $R^1$ is hydrogen or alkyl having from 1 to 2 carbon atoms, i.e. compounds of formula:

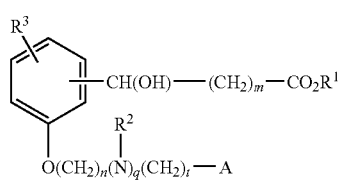

wherein A is described as above, can be prepared via reaction of scheme 2.

In the reaction scheme of Scheme 2, A, t, n, $R^3$ and $R^2$ are as above. Y is chloro or bromo and p is 1 to 3.

The compound of formula IX can be mesylated to furnish the compound of formula X via reaction of step (e). Any conventional conditions to carry out the mesylation reaction of a hydroxyl group can be utilized to carry out the step (e). The compound of formula X is then heated with the compound of formula XI to produce the compound of formula XII. Any of the conditions conventional to produce amino alcohol can be utilized to carry out the reaction of step (f).

In the compound of formula XII, alcohol can be displaced by chloro or bromo by treating the compound of formula XII with thionyl chloride, bromine, phosphorus tribromide and the like to produce the compound of formula XIII. Any conventional method to displace alcohol with chloro or bromo can be utilized to carry out the reaction of step (g).

The compound of formula XIII can be reacted with the compound of formula II via reaction of step (h) in the presence of a suitable base such as potassium carbonate, sodium hydride, triethylamine and the like. The reaction is carried out in conventional solvents such as dimethylformamide, tetrahydrofuran and the like to produce the corresponding compound of formula XIV. Any conventional method of etherification of a hydroxyl group in the presence of base (preferred base being potassium carbonate) can be utilized to carry out the reaction of step (h).

The compound of formula XIV can be converted to the compound of formula XV via reaction of step (i) by alkylating the compound of formula XIV with the compound of formula VI. This reaction is carried out in the presence of approximately a molar equivalent of a suitable base such as lithium hexamethyldisilane. This reaction is carried out in the same manner as described in connection with the reaction of step (c) of Scheme The compound of formula XV can be converted to the compound of XVI via reaction of step (j) by reducing the ketone group to an alcohol group. The reaction is carried out by utilizing a conventional reducing agent that converts ketone to alcohol. In carrying out this reaction it is generally preferred but not limited to utilize sodium borohydride as the reducing agent. Generally this reaction is carried out in solvents such as methanol, ethanol or the like. Generally the reaction is carried out at temperatures of from 0° C. to 25° C. The product can be isolated and purified by techniques such as extraction, evaporation, chromatography, and recrystallization.

Racemic mixtures of formula XVI can be separated by using HPLC. (Chirality 11:420-425 (1999)

The compound of formula XVI is the compound of formula I where $R^1$ is alkyl having from 1 to 2 carbon atoms.

The compound of formula XVI can be converted to the free acid by ester hydrolysis. Any conventional method of ester hydrolysis will produce the compound of formula I where $R^1$ is H.

$R^2$ is alkyl having from 1 to 3 carbon atoms and $R^1$ is alkyl having from 1 to 2 carbon atoms, i.e. compounds of formula:

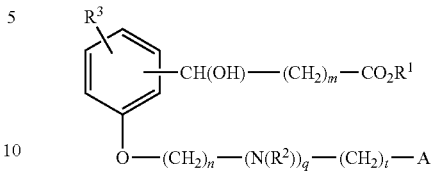

wherein A is described as above, can be prepared via reaction of scheme 3.

In the reaction scheme of Scheme 3, A, t, n, $R^3$ and $R^2$ are as above. $R^1$ is an alkyl group having from 1 to 2 carbon atoms.

Reaction Scheme 2

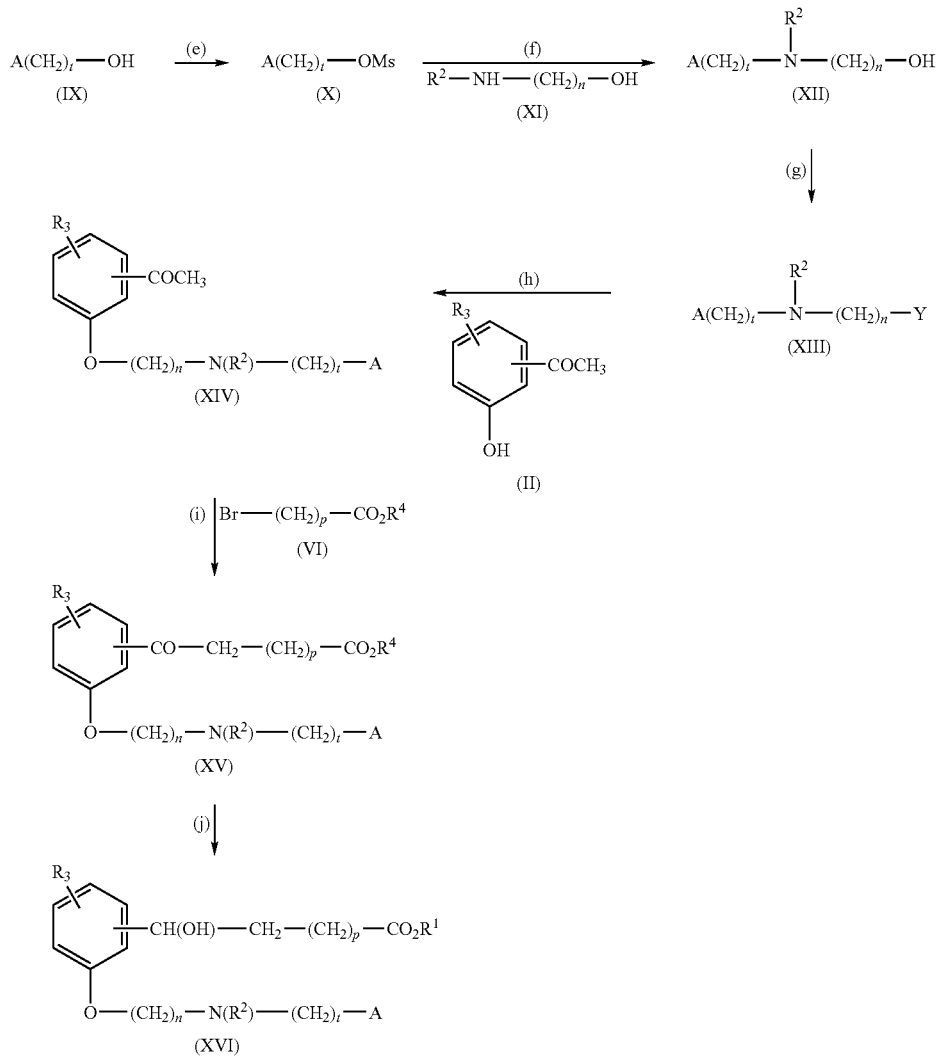

The compound of formula I where m is 1, q is 0 or 1, t is 0 or 1; and n is 1 or 2, $R^3$ is hydrogen, halo, alkoxy having from 1 to 3 carbon atoms or alkyl having from 1 to 3 carbon atoms, The compound of formula V (prepared in the same manner as described in the reaction of scheme 1) or XIV (prepared in the same manner as described in the reaction of scheme 2) can be reacted with dialkyl carbonate via reaction of step (k) in the presence of a suitable base such as sodium hydride and the like. The reaction can be carried out in conventional solvents such as N,N'-dimethylformamide, tetrahydrofuran, dichloromethane and the like followed by addition of dialkyl carbonate such as dimethyl or diethyl carbonate to produce the corresponding compound of formula XVII. Any conditions conventional in such alkylation reactions can be utilized to carry out the reaction of step (k).

The compound of formula XVII can be converted to the compound of formula XVIII via reaction of step (l) by reducing the beta-keto group to an alcohol group. The reaction can be carried out by utilizing a conventional reducing agent that converts ketone to alcohol. The reaction can be carried out by hydrogenation using a Raney nickel catalyst that had been treated with tartaric acid (Harada, T.; Izumi, Y. Chem Lett. 1978, 1195-1196) or hydrogenation with a chiral homogeneous ruthenium catalyst (Akutagawa, S.; Kitamura, M.; Kumobayashi, H.; Noyori, R.; Ohkuma, T.; Sayo, N.; Takaya, M. J. Am. Chem. Soc. 1987, 109, 5856-5858). The reduction can also be carried out by using sodium borohydride and the like. Generally this reaction is carried out in solvents such as methanol, ethanol and the like. Generally the reaction is carried out at temperatures of from 0° C. to 25° C. The product can be isolated and purified by techniques such as extraction, evaporation, chromatography, and recrystallization. Racemic mixtures of formula XVIII can be separated by using HPLC. (Chirality 11:420-425 (1999)

The compound of formula XVIII is the compound of formula I where m is 1 and $R^1$ is alkyl having from 1 to 2 carbon atoms.

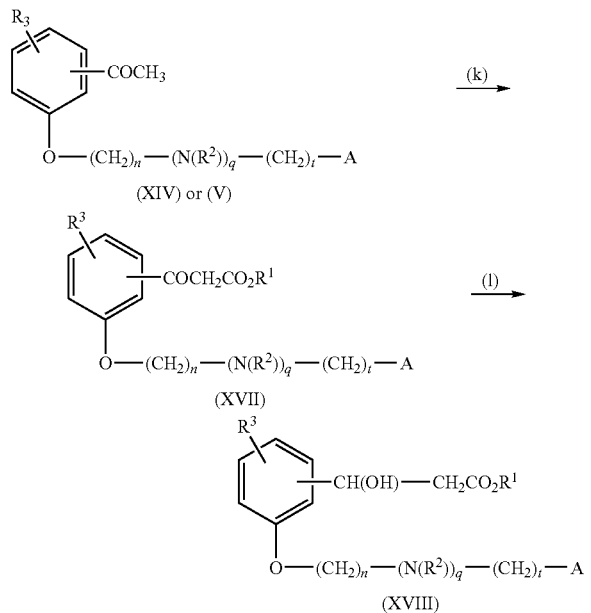

The compound of formula I where m is 0, q is 0 or 1, t is 0 or 1, and n is 1 or 2, $R^3$ is hydrogen, halo, alkoxy having from 1 to 3 carbon atoms or alkyl having from 1 to 3 carbon atoms, and $R^1$ is hydrogen or alkyl having from 1 to 2 carbon atoms, $R^2$ is alkyl having from 1 to 3 carbon atoms i.e. compounds of formula:

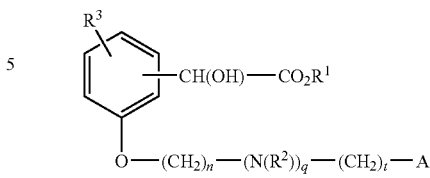

wherein A is described as above, can be prepared via reaction of scheme 4.

In the reaction of Scheme 4, t, n, A, $R^2$, $R^3$ and $R^1$ are as above.

The compound of formula V (prepared in the same manner as described in the reaction of scheme 1) or the compound of formula XVI (prepared in the same manner as described in the reaction of scheme 2) can be converted to the compound of formula XIX via reaction of step (m) by oxidation of methyl group with selenium dioxide in the presence of pyridine. Generally the reaction is carried out at temperatures of from 25° C.-100° C. The product can be isolated and purified by techniques such as extraction, evaporation, chromatography, and recrystallization.

The compound of formula XIX can be converted to compound of formula XX via reaction of step (n) by hydrogenation of alpha-keto acid using catalyst for example rhodium-{amidophosphine-phosphinite} (Tetrahedron: Asymmetry, Vol 8, No. 7, 1083-1099, 1997), [$Ru_2Cl_4(BINAP)_2$](NEt$_3$) (EP-A-0 295 890) and the like. Any conditions conventional in such hydrogenations can be utilized to carry out the reaction of step (n). Racemic mixtures of formula XX can be separated by using HPLC. (Chirality 11:420425 (1999).

The compound of formula XX is the compound of formula I where m is 0 and $R^1$ is H.

The compound of formula XX can be converted to compound of formula I where $R^1$ is alkyl having from 1 to 2 carbon atoms by esterification using methanol or ethanol. The reaction can be carried out either by using catalysts for example $H_2SO_4$, TsOH and the like or by using dehydrating agents for example dicyclohexylcarbodiimide and the like. Generally the reaction is carried out in solvents such as N,N'-dimethylformamide, tetrahydrofuran, dichloromethane or the like. Generally the reaction is carried out at temperatures of from 0° C. to 100° C. The product can be isolated and purified by techniques such as extraction, evaporation, chromatography, and recrystallization.

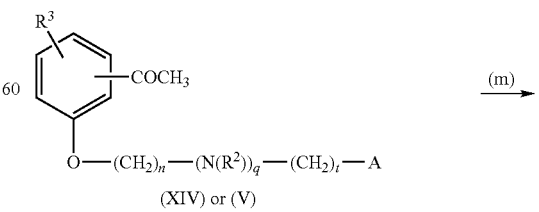

-continued

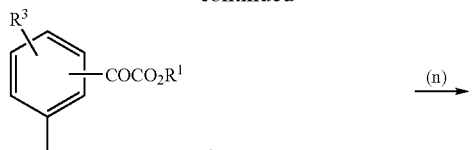
(XIX)

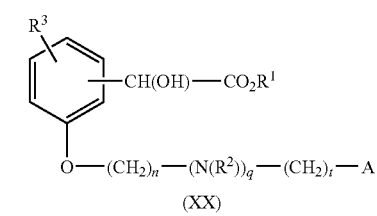
(XX)

The compound of formula I where m is 0, q is 0 or 1, t is 0 or 1, and n is 1 or 2, $R^3$ is hydrogen, halo, alkoxy having from 1 to 3 carbon atoms or alkyl having from 1 to 3 carbon atoms, and $R^1$ is hydrogen or alkyl having from 1 to 2 carbon atoms, $R^2$ is alkyl having from 1 to 3 carbon atoms i.e. compounds of formula:

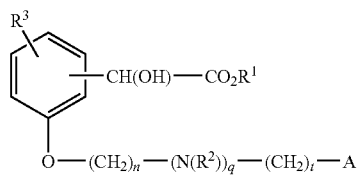

can also be prepared from the compound of formula XXI,

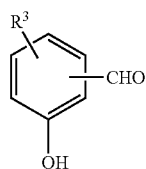

wherein $R^3$ is hydrogen, halo, alkoxy having from 1 to 3 carbon atoms or alkyl having from 1 to 3 carbon atoms via reaction of scheme 5.

In the reaction of Scheme 5, t, n, A, $R^2$, $R^3$ and $R^1$ are as above. Y is chloro or bromo.

The compound of formula XXI can be converted to compound of formula XXII via reaction of step (O) by reaction with compound of formula III or with the compound of formula IV (prepared in the same manner as described in the reaction of scheme 1) or with the compound of formula XIII (prepared in the same manner as described in the reaction of scheme 2). These reactions can be carried out in the same manner as described in connection with reaction steps of (a), (b) or (h). The compound of formula XXII can be converted to the compound of formula XXIII via reaction of step (p) by reaction with NaCN or KCN in the presence of $NaHSO_3$ and water followed by hydrolysis to give compound of formula XXIII. (Organic Syntheses; Wiley: New York, 1941; Collect. Vol. 1, p 336.)

The compound of formula XXII can be converted directly to the compound of formula XXIII via reaction of step (q) by reaction in the presence of a suitable catalyst for example triethylbenzylammonium chloride and the like. Generally the reaction is carried out in solvents such as chloroform-aq sodium hydroxide. Generally the reaction is carried out at temperatures of from 25° C. to 100° C. (Synthesis 1974, 724-725) Racemic mixtures of formula XXIII can be separated by using HPLC. (Chirality 11:420-425 (1999)

The compound of formula XXIII is the compound of formula I where m is 0 and $R^1$ is H.

The compound of formula XXIII can be converted to compound of formula I where $R^1$ is alkyl having from 1 to 2 carbon atoms by esterification using methanol or ethanol. The reaction can be carried out either by using catalysts for example $H_2SO_4$, TsOH and the like or by using dehydrating agents for example dicyclohexylcarbodiimide and the like. Generally the reaction is carried out in solvents such as N, N'-dimethylformamide, tetrahydrofuran, dichloromethane or the like. Generally the reaction is carried out at temperatures of from 0° C. to 100° C. The product can be isolated and purified by techniques such as extraction, evaporation, chromatography, and recrystallization.

Reaction Scheme 5

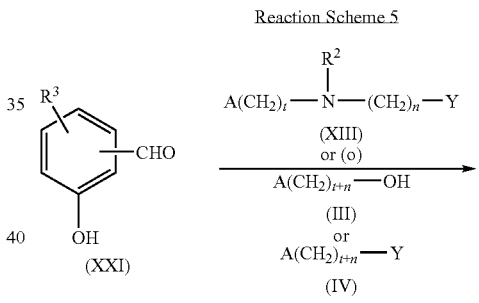

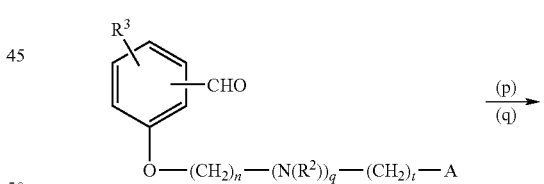
(XXII)

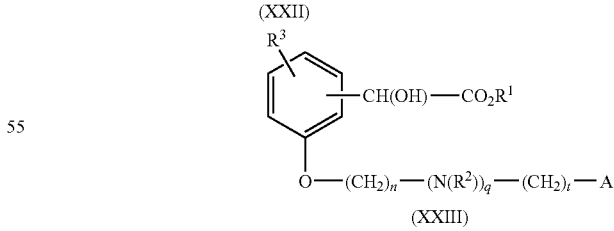
(XXIII)

The compound of formula III, $A(CH_2)_{t+n}$—OH and the compound of formula IV, where t is 0 or 1, n is 1 or 2, i.e. compounds of formula:

$A(CH_2)_{t+n}$—Y wherein A is described as above, and Y is a leaving group, can be prepared via reaction of scheme 6.

In the reaction of Scheme 6, A is described as above and Y is a leaving group. The compound of formula XXIV can be reduced to the compound of formula XXV via reaction of step (r). The reaction is carried out utilizing a conventional reducing agent for example alkali metal hydride such as lithium aluminum hydride. The reaction is carried out in a suitable solvent, such as tetrahydrofuran. Any of the conditions conventional in such reduction reactions can be utilized to carry out the reaction of step (r).

The compound of formula XXV is the compound of formula III where t is 0 and n is 1.

The compound of formula XXV can be converted to the compound of formula XXVI by displacing hydroxyl group with a halogen group preferred halogen being bromo or chloro. Appropriate halogenating reagents include but are not limited to thionyl chloride, bromine, phosphorous tribromide, carbon tetrabromide and the like. Any conditions conventional in such halogenation reactions can be utilized to carry out the reaction of step (s).

The compound of formula XXVI is the compound of formula IV where t is 0 and n is 1.

The compound of formula XXVI can be converted to the compound of formula XXVII by reacting XXVI with an alkali metal cyanide for example sodium or potassium cyanide. The reaction is carried out in a suitable solvent, such as dimethyl sulfoxide. Any of the conditions conventionally used in the preparation of nitrile can be utilized to carry out the reaction of step (t).

The compound of formula XXVII can be converted to the compound of formula XXVIII via reaction step (u) by acid or base hydrolysis. In carrying out this reaction it is generally preferred to utilize basic hydrolysis, for example aqueous sodium hydroxide. Any of the conditions conventionally used in hydrolysis of nitrile can be utilized to carry out the reaction of step (u).

The compound of formula XXVIII can be reduced to give the compound of formula XXIX via reaction of step (v). This reaction can be carried out in the same manner as described hereinbefore in the reaction of step (r).

The compound of formula XXIX is the compound of formula III where t is 1 and n is 1.

The compound of formula XXIX can be converted to the compound of formula XXX via reaction of step (w) in the same manner as described hereinbefore in connection with the reaction of step (s).

The compound of formula XXX is the compound of formula IV where t is 1 and n is 1.

The compound of formula XXX can be reacted with diethyl malonate utilizing a suitable base for example sodium hydride to give compound of formula XXXI. The reaction is carried out in suitable solvents, such as dimethylformamide, tetrahydrofuran and the like. Any of the conditions conventional in such alkylation reactions can be utilized to carry out the reaction of step (x).

The compound of formula XXXI can be hydrolyzed by acid or base to give compound of formula XXXII via reaction of step (y).

The compound of formula XXXII can be converted to the compound of formula XXXIII via reaction of step (z) in the same manner as described hereinbefore in connection with the reaction of step (r).

The compound of formula XXIII is the compound of formula III where t is 1 and n is 2.

The compound of formula XXXIII can be converted to the compound of formula XXXIV via reaction of step (a') in the same manner as described hereinbefore in connection with the reaction of step (s).

The compound of formula XXXIV is the compound of formula IV where t is 1 and n is 2.

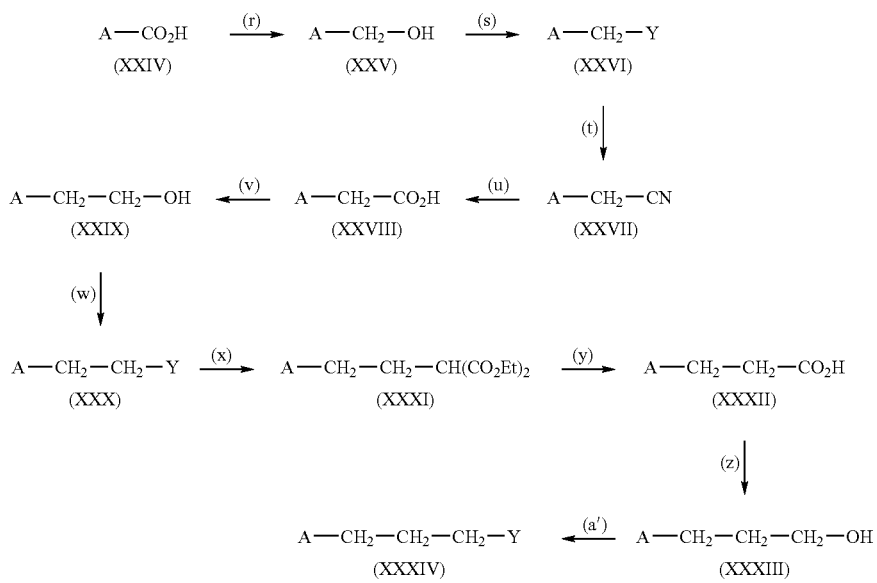

Reaction Scheme 6

The compound of formula II where $R^3$ is halo, alkoxy having from 1 to 3 carbon atoms or 6 alkyl having from 1 to 3 carbon atoms, i.e. compounds of formula:

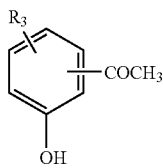

can be prepared via reaction of scheme 7.

In the reaction of Scheme 7, $R^1$ is H and $R^3$ is halo, alkoxy having from 1 to 3 carbon atoms or alkyl having from 1 to 3 carbon atoms.

The compound of formula II can be synthesized according to the method of George M Rubottom et al., J. Org. Chem. 1983, 48, 1550-1552.

Reaction Scheme 7

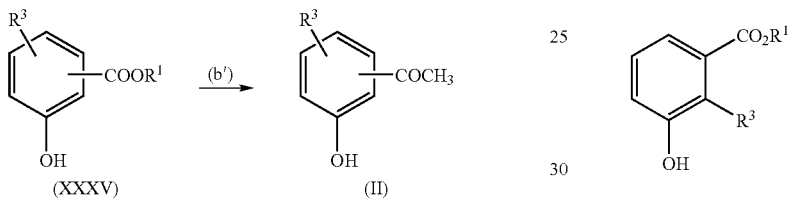

The compound of formula XXXV where $R^1$ is H and $R^3$ is halo, i.e. compounds of formula:

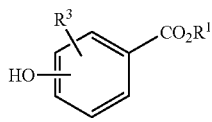

are either commercially available or can be prepared according to the methods described in the literature as follows:
1. 3-Br or F-2-OHC$_6$H$_3$CO$_2$H
Canadian Journal of Chemistry (2001), 79(11) 1541-1545.
2. 4-Br-2-OHC$_6$H$_3$CO$_2$H
WO 9916747 or JP 04154773.
3. 2-Br-6-OHC$_6$H$_3$CO$_2$H
JP 47039101.
4. 2-Br-3-OHC$_6$H$_3$CO$_2$H
WO 9628423.
5. 4-Br-3-OHC$_6$H$_3$CO$_2$H
WO 2001002388.
6. 3-Br-5-OHC$_6$H$_3$CO$_2$H
Journal of labelled Compounds and Radiopharmaceuticals (1992), 31 (3), 175-82.
7. 2-Br-5-OHC$_6$H$_3$CO$_2$H and 3-Cl-4-OHC$_6$H$_3$CO$_2$H
WO 9405153 and U.S. Pat. No. 5,519,133.
8. 2-Br-4-OHC$_6$H$_3$CO$_2$H and 3-Br-4-OHC$_6$H$_3$CO$_2$H
WO 20022018323
9. 2-Cl-6-OHC$_6$H$_3$CO$_2$H
JP 06293700
10. 2-Cl-3-OHC$_6$H$_3$CO$_2$H
Proceedings of the Indiana Academy of Science (1983), Volume date 1982, 92, 145-51.
11. 3-Cl-5-OHC$_6$H$_3$CO$_2$H
WO 2002000633 and WO 2002044145.
12. 2-Cl-5-OHC$_6$H$_3$CO$_2$H
WO 9745400.
13. 5-I-2-OHC$_6$H$_3$CO$_2$H and 3-I, 2-OHC$_6$H$_3$CO$_2$H
Z. Chem. (1976), 16(8), 319-320.
14. 4-I-2-OHC$_6$H$_3$CO$_2$H
Journal of Chemical Research, Synopses (1994), (11), 405.
15. 6-I-2-OHC$_6$H$_3$CO$_2$H
U.S. Pat. No. 4,93,2999.
16. 2-I-3-OHC$_6$H$_3$CO$_2$H and 4-I-3-OHC$_6$H$_3$CO$_2$H
WO 9912928.
17. 5-I-3-OHC$_6$H$_3$CO$_2$H
J. Med. Chem. (1973), 16(6), 684-7.
18. 2-I-4-OHC$_6$H$_3$CO$_2$H
Collection of Czechoslovak Chemical Communications, (1991), 56(2), 459-77.
19. 3-I-4-OHC$_6$H$_3$CO$_2$,
J.O.C. (1990), 55(18), 5287-91.

The compound of formula XXXV, where $R^1$ is H and $R^3$ is alkoxy having from 1 to 3 carbon atoms, i.e. compounds of formula:

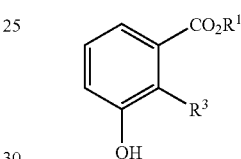

can be synthesized via the reaction of scheme 8.

In the reaction of Scheme 8, $R^1$ and $R^3$ are as above, and $R^4$ is alkyl group having from 1 to 2 carbon atoms.

The compound of formula XXXVI can be converted to the compound of formula XXXVII by reducing the aldehyde to primary alcohol. In carrying out this reaction, it is preferred but not limited to use sodium borohydride as the reducing reagent. Any of the conditions suitable in such reduction reactions can be utilized to carry out the reaction of step (c').

The compound of formula XXXVII can be converted to the compound of formula XXXVIII via reaction of step (d') by protecting 1-3 Diols by using 1,1,3,3-Tetraisopropyldisiloxane. The suitable conditions for this protecting group can be described in the Protecting Groups in Organic Synthesis by T. Greene.

The compound of formula XXXVIII can be converted to the compound of formula XXXIX via reaction of step (e') by protecting the phenol group using benzyl bromide. The suitable conditions for this protecting group can be described in the Protecting Groups in Organic Synthesis by T. Greene.

The compound of formula XXXIX can be converted to the compound of formula XL by deprotection using tetrabutylammonium fluoride via reaction of step (f). The suitable conditions for the deprotection can be described in the Protecting Groups in Organic Synthesis by T. Greene.

The compound of formula XL can be converted to compound of formula XLI via reaction of step (g') by oxidation. Any conventional oxidizing group that converts primary alcohol to an acid for example chromium oxide and the like can be utilized to carry out the reaction of step (g').

The compound of formula XLI can be converted to the compound of formula XLII by esterification of compound of formula XLI with methanol or ethanol. The reaction can be carried out either by using catalysts for example H$_2$SO$_4$, TsOH and the like or by using dehydrating agents for example dicyclohexylcarbodiimide and the like. Any of the conditions conventional in such esterification reactions can be utilized to carry out the reaction of step (h').

The compound of formula XLII can be converted to the compound of formula XLIII by etherifying or alkylating the compound of formula XLII with methyl halide or ethyl halide or propyl halide by using suitable base for example potassium carbonate, sodium hydride and the like. The reaction is carried out in conventional solvents, such as tetrahydrofuran, dimethylformamide. The reaction is generally carried out at temperatures of from 0° C. to 40° C. Any of the conditions suitable in such alkylation reactions can be utilized to carry out the reaction of step (i').

The compound of formula XLIII can be converted to compound of formula XLIV via reaction of step (j') by deprotection of ester and benzyl groups. The suitable deprotecting conditions can be described in the Protecting Groups in Organic Synthesis by T. Greene.

1. 2-OMe-4-OHC$_6$H$_3$CO$_2$H
U.S. 2001034343 or WO 9725992.
2. 5-OMe-3-OHC$_6$H$_3$CO$_2$H
J.O.C (2001), 66(23), 7883-88.
3. 2-OMe-5-OHC$_6$H$_3$CO$_2$H
U.S. Pat. No. 6,194,406 (Page 96) and Journal of the American Chemical Society (1985), 107(8), 2571-3.
4. 3-OEt-5-OHC$_6$H$_3$CO$_2$H
Taiwan Kexue (1996), 49(1), 51-56.
5. 4-OEt-3-OHC$_6$H$_3$CO$_2$H
WO 9626176
6. 2-OEt-4-OHC$_6$H$_3$CO$_2$H
Takeda Kenkyusho Nempo (1965), 24,221-8.
JP 07070025.
7. 3-OEt-4-OHC$_6$H$_3$CO$_2$H
WO 9626176.
8. 3-OPr-2-OHC$_6$H$_3$CO$_2$H
JP 07206658, DE 2749518.

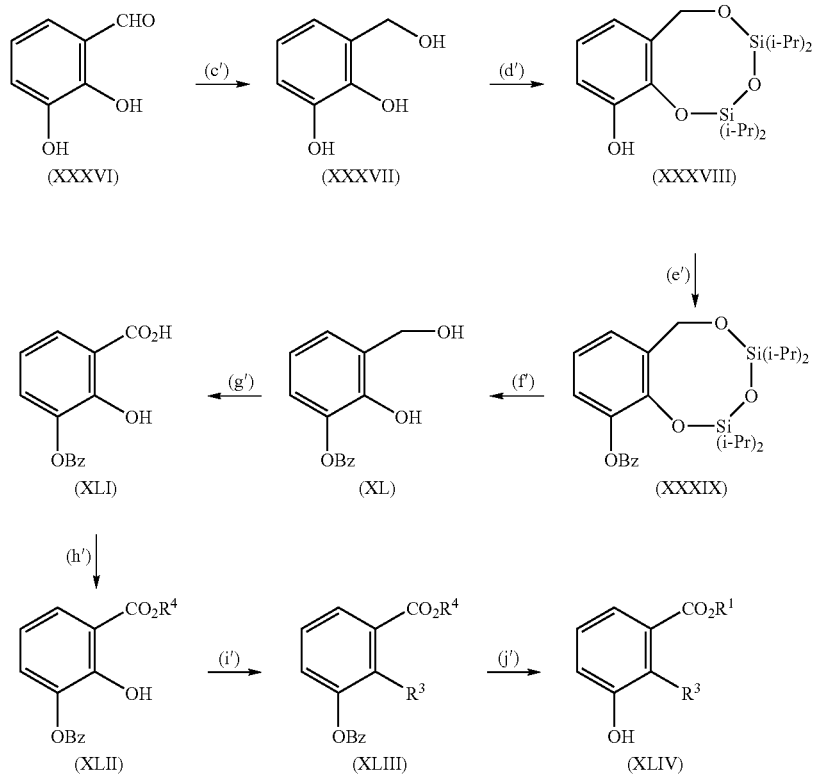

The compound of formula XXXV, where R$^1$ is H and R$^3$ is alkoxy having from 1 to 3 carbon atoms, i.e. compounds of formula:

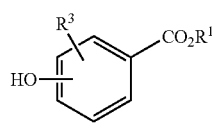

are either commercially available or can be prepared according to the methods described in the literature as follows:

9. 4-OPr-2-OHC$_6$H$_3$CO$_2$H
Farmacia (Bucharest) (1970), 18(8), 461-6.
JP 08119959.
10. 2-OPr-5-OHC$_6$H$_3$CO$_2$H and 2-OEt-5-OHC$_6$H$_3$CO$_2$H
Adapt synthesis from U.S. Pat. No. 6,194,406 (Page 96) by using propyl iodide and ethyl iodide.
11. 4—OPr-3-OHC$_6$H$_3$CO$_2$H
Adapt synthesis from WO 9626176
12. 2-OPr-4-OHC$_6$H$_3$CO$_2$H
Adapt synthesis from Takeda Kenkyusho Nempo (1965), 24,221-8 by using propyl halide.
13. 4-OEt-3-OHC$_6$H$_3$CO$_2$H Biomedical Mass Spectrometry (1985), 12(4), 163-9.

14. 3-OPr-5-OHC$_6$H$_3$CO$_2$H

Adapt synthesis from Taiwan Kexue (1996), 49(1), 51-56 by using propyl halide.

The compound of formula XXXV, where R$^1$ is H and R$^3$ is an alkyl having from 1 to 3 carbon atoms, i.e. compounds of formula:

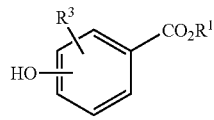

are either commercially available or can be prepared according to the methods described in the literature as follows:
1. 5-Me-3-OHC$_6$H$_3$CO$_2$H and 2-Me-5-OHC$_6$H$_3$CO$_2$H
WO 9619437.
J.O.C. 2001, 66, 7883-88.
2. 2-Me-4-OHC$_6$H$_3$CO$_2$H
WO 8503701.
3. 3-Et-2-OHC$_6$H$_3$CO$_2$H and 5-Et-2-OHC$_6$H$_3$CO$_2$H
J. Med. Chem. (1971), 14(3), 265.
4. 4-Et-2-OHC$_6$H$_3$CO$_2$H
Yaoxue Xuebao (1998), 33(1), 67-71.
5. 2-Et-6-OHC$_6$H$_3$CO$_2$H and 2-n-Pr-6-OHC$_6$H$_3$CO$_2$H
J. Chem. Soc., Perkin Trans 1 (1979), (8), 2069-78.
6. 2-Et-3-OHC$_6$H$_3$CO$_2$H
JP 10087489 and WO 9628423.
7. 4-Et-3-OHC$_6$H$_3$CO$_2$H J.O.C. 2001, 66,7883-88.
WO 9504046.
8. 2-Et-5-OHC$_6$H$_3$CO$_2$H
J.A.C.S (1974), 96(7), 2121-9.
9. 2-Et-4-OHC$_6$H$_3$CO$_2$H and 3-Et-4-OHC$_6$H$_3$CO$_2$H
JP 04282345.
10. 3-n-Pr-2-OHC$_6$H$_3$CO$_2$H
J.O.C (1991), 56(14), 4525-29.
11. 4-n-Pr-2-OHC$_6$H$_3$CO$_2$H
EP 279630.
12. 5-n-Pr-2-OHC$_6$H$_3$CO$_2$H
J. Med. Chem (1981), 24(10), 1245-49
13. 2-n-Pr-3-OHC$_6$H$_3$CO$_2$H
WO 9509843 and WO 9628423.
14. 4-n-Pr-3-OHC$_6$H$_3$CO$_2$H WO 9504046.
15. 2-n-Pr-5-OHC$_6$H$_3$CO$_2$H
Synthesis can be adapted from J.A.C.S (1974), 96(7), 2121-9 by using ethyl alpha formylvalerate.
16. 3-n-Pr-4-OHC$_6$H$_3$CO$_2$H Polymer (1991),32(11) 2096-105.
17. 2-n-Pr-4-OHC$_6$H$_3$CO$_2$H 3-Propylphenol can be methylated to 3-Propylanisole, which was then formylated to 4-Methoxy-3-benzaldehyde. The aldehyde can be oxidized by Jone's reagent to give corresponding acid and deprotection of methyl group by BBr$_3$ will give the title compound.
18. 1. 3-Et-5-OHC$_6$H$_3$CO$_2$H and 3-Pr-n-5-OHC$_6$H$_3$CO$_2$H Adapt synthesis from J.O.C. 2001, 66,7883-88 by using 2-Ethylacrolein and 2-Propylacrolein.

The compound of formula XXI where R$^3$ is hydrogen, halo, alkoxy having from 1 to 3 carbon atoms or alkyl having from 1 to 3 carbon atoms, i.e. compounds of formula:

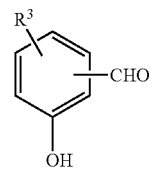

can be prepared via reaction of scheme 9.

In the reaction scheme of Scheme 9, R$^4$ is alkyl group having from 1 to 2 carbon atoms, and P is a protecting group.

The compound of formula XLV can be converted to the compound of formula XLVI via the reaction of step (k') by protecting the hydroxy group and then deprotecting the ester group by utilizing suitable protecting and deprotecting groups such as those described in Protecting Groups in Organic Synthesis by T. Greene.

The compound of formula XLVI can be converted to the compound of formula XLVII via reaction of step (l') by reducing acid group to alcohol group. The reaction can be carried out utilizing a conventional reducing agent for example alkali metal hydride such as lithium aluminum hydride. The reaction can be carried out in a suitable solvent, such as tetrahydrofuran. Any of the conditions conventional in such reduction reactions can be utilized to carry out the reaction of step (l').

The compound of formula XLVII can be converted to the compound of formula XLVIII via reaction of step (m') by oxidation of alcohol to the aldehyde. The reaction can be carried out utilizing a suitable oxidizing agent for example pyridinium chlorochromate, or dimethyl sulfoxide activated by 2,4,6-trichloro[1,3,5]-triazine (cyanuric chloride, TCT) under Swern oxidation conditions (J.O.C. 2001, 66, 7907-7909) and the like. Any of the conditions conventional in such oxidation reactions can be utilized to carry out the reaction of step (m').

In the compound of formula XLVIII, the hydroxy group can be deprotected via reaction of step (n') by suitable deprotecting reagents such as those described in Protecting Groups in Organic Synthesis by T. Greene to give the compound of formula XXI.

Reaction Scheme 9

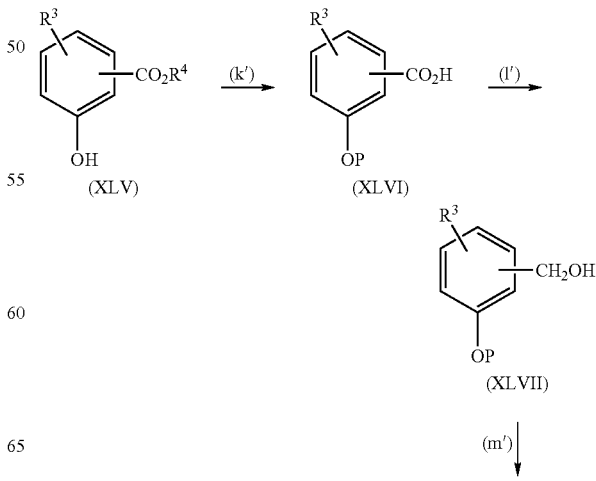

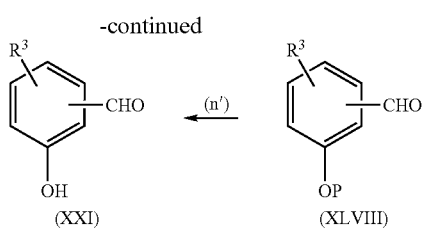

(XXI)   (XLVIII)

The compound of formula XLV where $R^4$ is alkyl group having from 1 to 2 carbon atoms and $R^3$ is halo, alkoxy having from 1 to 3 carbon atoms or alkyl having from 1 to 3 carbon atoms, i.e. compounds of formula:

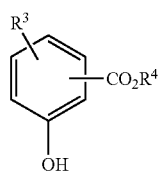

can be prepared via reaction of scheme 10.

In the reaction of Scheme 10, $R^1$ is H. $R^3$ and $R^4$ are as above.

The compound of formula XXXV can be converted to the compound of formula XLV via reaction of step (o') by esterification of compound of formula XXXV with methanol or ethanol. The reaction can be carried out either by using catalysts for example $H_2SO_4$, TsOH and the like or by using dehydrating agents for example dicyclohexylcarbodiimide and the like. Any of the conditions conventional in such esterification reactions can be utilized to carry out the reaction of step (o').

Reaction Scheme 10

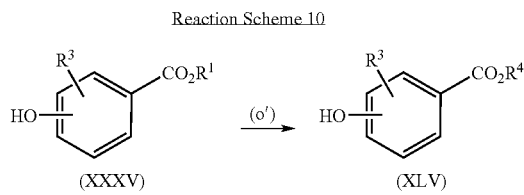

(XXXV)   (XLV)

Use in Methods of Treatment

This invention provides a method for treating a mammalian subject with a condition selected from the group consisting of insulin resistance syndrome and diabetes (both primary essential diabetes such as Type I Diabetes or Type II Diabetes and secondary nonessential diabetes), comprising administering to the subject an amount of a biologically active agent as described herein effective to treat the condition. In accordance with the method of this invention a symptom of diabetes or the chance of developing a symptom of diabetes, such as atherosclerosis, obesity, hypertension, hyperlipidemia, fatty liver disease, nephropathy, neuropathy, retinopathy, foot ulceration and cataracts, each such symptom being associated with diabetes, can be reduced. This invention also provides a method for treating hyperlipidemia comprising administering to the subject an amount of a biologically active agent as described herein effective to treat the condition. As shown in the Examples, compounds reduce serum triglycerides and free fatty acids in hyperlipidemic animals. This invention also provides a method for treating cachexia comprising administering to the subject an amount of a biologically active agent as described herein effective to treat the cachexia. This invention also provides a method for treating obesity comprising administering to the subject an amount of a biologically active agent as described herein effective to treat the condition. This invention also provides a method for treating a condition selected from atherosclerosis or arteriosclerosis comprising administering to the subject an amount of a biologically active agent as described herein effective to treat the condition. The active agents of this invention are effective to treat hyperlipidemia, fatty liver disease, cachexia, obesity, atherosclerosis or arteriosclerosis whether or not the subject has diabetes or insulin resistance syndrome. The agent can be administered by any conventional route of systemic administration. Preferably the agent is administered orally. Accordingly, it is preferred for the medicament to be formulated for oral administration. Other routes of administration that can be used in accordance with this invention include rectally, parenterally, by injection (e.g. intravenous, subcutaneous, intramuscular or intraperitioneal injection), or nasally.

Further embodiments of each of the uses and methods of treatment of this invention comprise administering any one of the embodiments of the biologically active agents described above. In the interest of avoiding unnecessary redundancy, each such agent and group of agents is not being repeated, but they are incorporated into this description of uses and methods of treatment as if they were repeated.

Many of the diseases or disorders that are addressed by the compounds of the invention fall into two broad categories: Insulin resistance syndromes and consequences of chronic hyperglycemia. Dysregulation of fuel metabolism, especially insulin resistance, which can occur in the absence of diabetes (persistent hyperglycemia) per se, is associated with a variety of symptoms, including hyperlipidemia, atherosclerosis, obesity, essential hypertension, fatty liver disease (NASH; nonalcoholic steatohepatitis), and, especially in the context of cancer or systemic inflammatory disease, cachexia. Cachexia can also occur in the context of Type I Diabetes or late-stage Type II Diabetes. By improving tissue fuel metabolism, active agents of the invention are useful for preventing or ameliorating diseases and symptoms associated with insulin resistance, as is demonstrated in animals in the Examples. While a cluster of signs and symptoms associated with insulin resistance may coexist in an individual patient, it many cases only one symptom may dominate, due to individual differences in vulnerability of the many physiological systems affected by insulin resistance. Nonetheless, since insulin resistance is a major contributor to many disease conditions, drugs which address this cellular and molecular defect are useful for prevention or amelioration of virtually any symptom in any organ system that may be due to, or exacerbated by, insulin resistance.

When insulin resistance and concurrent inadequate insulin production by pancreatic islets are sufficiently severe, chronic hyperglycemia occurs, defining the onset of Type II diabetes mellitus (NIDDM). In addition to the metabolic disorders related to insulin resistance indicated above, disease symptoms secondary to hyperglycemia also occur in patients with NIDDM. These include nephropathy, peripheral neuropathy, retinopathy, microvascular disease, ulceration of the extremities, and consequences of nonenzymatic glycosylation of proteins, e.g. damage to collagen and other connective tissues. Attenuation of hyperglycemia reduces the rate of onset and severity of these consequences of diabetes. Because, as is demonstrated in the Examples, active agents and compositions of the invention help to reduce hyperglycemia in diabetes, they are useful for prevention and amelioration of complications of chronic hyperglycemia.

Both human and non-human mammalian subjects can be treated in accordance with the treatment method of this invention. The optimal dose of a particular active agent of the invention for a particular subject can be determined in the clinical setting by a skilled clinician. In the case of oral administration to a human for treatment of disorders related to insulin resistance, diabetes, hyperlipidemia, fatty liver disease, cachexia or obesity the agent is generally administered in a daily dose of from 1 mg to 400 mg, administered once or twice per day. In the case of oral administration to a mouse the agent is generally administered in a daily dose from 1 to 300 mg of the agent per kilogram of body weight. Active agents of the invention are used as monotherapy in diabetes or insulin resistance syndrome, or in combination with one or more other drugs with utility in these types of diseases, e.g. insulin releasing agents, prandial insulin releasers, biguanides, or insulin itself. Such additional drugs are administered in accord with standard clinical practice. In some cases, agents of the invention will improve the efficacy of other classes of drugs, permitting lower (and therefore less toxic) doses of such agents to be administered to patients with satisfactory therapeutic results. Established safe and effective dose ranges in humans for representative compounds are: metformin 500 to 2550 mg/day; glyburide 1.25 to 20 mg/day; GLUCOVANCE (combined formulation of metformin and glyburide) 1.25 to 20 mg/day glyburide and 250 to 2000 mg/day metformin; atorvastatin 10 to 80 mg/day; lovastatin 10 to 80 mg/day; pravastatin 10 to 40 mg/day; and simvastatin 5-80 mg/day; clofibrate 2000 mg/day; gemfibrozil 1200 to 2400 mg/day, rosiglitazone 4 to 8 mg/day; pioglitazone 15 to 45 mg/day; acarbose 75-300 mg/day; repaglinide 0.5 to 16 mg/day.

Type I Diabetes Mellitus: A patient with Type I diabetes manages their disease primarily by self-administration of one to several doses of insulin per day, with frequent monitoring blood glucose to permit appropriate adjustment of the dose and timing of insulin administration. Chronic hyperglycemia leads to complications such as nephropathy, neuropathy, retinopathy, foot ulceration, and early mortality; hypoglycemia due to excessive insulin dosing can cause cognitive dysfunction or unconsciousness. A patient with Type I diabetes is treated with 1 to 400 mg/day of an active agent of this invention, in tablet or capsule form either as a single or a divided dose. The anticipated effect will be a reduction in the dose or frequency of administration of insulin required to maintain blood glucose in a satisfactory range, and a reduced incidence and severity of hypoglycemic episodes. Clinical outcome is monitored by measurement of blood glucose and glycosylated hemoglobin (an index of adequacy of glycemic control integrated over a period of several months), as well as by reduced incidence and severity of typical complications of diabetes. A biologically active agent of this invention can be administered in conjunction with islet transplantation to help maintain the anti-diabetic efficacy of the islet transplant.

Type II Diabetes Mellitus: A typical patient with Type II diabetes (NIDDM) manages their disease by programs of diet and exercise as well as by taking medications such as metformin, glyburide, repaglinide, rosiglitazone, or acarbose, all of which provide some improvement in glycemic control in some patients, but none of which are free of side effects or eventual treatment failure due to disease progression. Islet failure occurs over time in patients with NIDDM, necessitating insulin injections in a large fraction of patients. It is anticipated that daily treatment with an active agent of the invention (with or without additional classes of antidiabetic medication) will improve glycemic control, reduce the rate of islet failure, and reduce the incidence and severity of typical symptoms of diabetes. In addition, active agents of the invention will reduce elevated serum triglycerides and fatty acids, thereby reducing the risk of cardiovascular disease, a major cause of death of diabetic patients. As is the case for all other therapeutic agents for diabetes, dose optimization is done in individual patients according to need, clinical effect, and susceptibility to side effects.

Hyperlipidemia: Elevated triglyceride and free fatty acid levels in blood affect a substantial fraction of the population and are an important risk factor for atherosclerosis and myocardial infarction. Active agents of the invention are useful for reducing circulating triglycerides and free fatty acids in hyperlipidemic patients. Hyperlipidemic patients often also have elevated blood cholesterol levels, which also increase the risk of cardiovascular disease. Cholesterol-lowering drugs such as HMG-CoA reductase inhibitors ("statins") can be administered to hyperlipidemic patients in addition to agents of the invention, optionally incorporated into the same pharmaceutical composition.

Fatty Liver Disease: A substantial fraction of the population is affected by fatty liver disease, also known as nonalcoholic steatohepatitis (NASH); NASH is often associated with obesity and diabetes. Hepatic steatosis, the presence of droplets of triglycerides with hepatocytes, predisposes the liver to chronic inflammation (detected in biopsy samples as infiltration of inflammatory leukocytes), which can lead to fibrosis and cirrhosis. Fatty liver disease is generally detected by observation of elevated serum levels of liver-specific enzymes such as the transaminases ALT and AST, which serve as indices of hepatocyte injury, as well as by presentation of symptoms which include fatigue and pain in the region of the liver, though definitive diagnosis often requires a biopsy. The anticipated benefit is a reduction in liver inflammation and fat content, resulting in attenuation, halting, or reversal of the progression of NASH toward fibrosis and cirrhosis.

Pharmaceutical Compositions

This invention provides a pharmaceutical composition comprising a biologically active agent as described herein and a pharmaceutically acceptable carrier. Further embodiments of the pharmaceutical composition of this invention comprise any one of the embodiments of the biologically active agents described above. In the interest of avoiding unnecessary redundancy, each such agent and group of agents is not being repeated, but they are incorporated into this description of pharmaceutical compositions as if they were repeated.

Preferably the composition is adapted for oral administration, e.g. in the form of a tablet, coated tablet, dragee, hard or soft gelatin capsule, solution, emulsion or suspension. In general the oral composition will comprise from 1 mg to 400 mg of such agent. It is convenient for the subject to swallow one or two tablets, coated tablets, dragees, or gelatin capsules per day. However the composition can also be adapted for administration by any other conventional means of systemic administration including rectally, e.g. in the form of suppositories, parenterally, e.g. in the form of injection solutions, or nasally.

The biologically active compounds can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils and the like. Suitable carriers for suppositories are, for example, natural or hardened oils, waxes, fats, semil-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances, particularly antidiabetic or hypolipidemic agents that act through mechanisms other than those underlying the effects of the compounds of the invention. Agents which can advantageously be combined with compounds of the invention in a single formulation include but are not limited to biguanides such as metformin, insulin releasing agents such as the sulfonylurea insulin releaser glyburide and other sulfonylurea insulin releasers, cholesterol-lowering drugs such as the "statin" HMG-CoA reductase inhibitors such as atrovastatin, lovastatin, pravastatin and simvastatin, PPAR-alpha agonists such as clofibrate and gemfibrozil, PPAR-gamma agonists such as thiazolidinediones (e.g. rosiglitazone and pioglitazone, alpha-glucosidase inhibitors such as acarbose (which inhibit starch digestion), and prandial insulin releasers such as repaglinide. The amounts of complementary agents combined with compounds of the invention in single formulations are in accord with the doses used in standard clinical practice. Established safe and effective dose ranges for certain representative compounds are set forth above.

The invention will be better understood by reference to the following examples which illustrate but do not limit the invention described herein.

CHEMICAL SYNTHESIS EXAMPLES

Example 1

4-(3-(2,6-Dimethylbenzyloxy)-phenyl)-4(R)-hydroxybutanoic acid

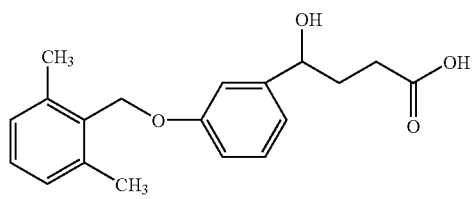

Step A: Preparation of 4-(3-(2,6-Dimethylbenzyloxy)-phenyl)-4(R)-hydroxybutanoic acid To a stirred solution of 4-(3-(2,6-Dimethylbenzyloxy)phenyl)-4-oxobutyric acid (WO 02/100341, 3 g, 9.6 mmol) in methanol (64 ml) was added cerium chloride (3.55 g, 14.4 mmol). The reaction mixture was stirred for 10 minutes at room temperature, cooled to 0° C., and NaBH$_4$ (0.400 g, 10.6 mmol) was added. The stirring continued at 0° C. for 4 hours, and the reaction was quenched with few drops of 50% aqueous acetic acid. Water (60 ml) and chloroform (60 ml) were added, and the reaction mixture was extracted with chloroform (3×25 ml). The organic layer was washed with water (2×) and brine (2×). The combined organic layer was dried over Na$_2$SO$_4$, filtered, concentrated and purified by flash column chromatography using chloroform:methanol (95:5 spiked with acetic acid) to give the title compound as white solid.

$^1$H NMR (270 MHz, CDCl$_3$): 2.1 (q, 2H); 2.4 (s, 6H); 2.5 (t, 2H); 4.8 (t, 1H); 5.1 (s, 2H); 6.9-7.1 (m, 4H); 7.15-7.3 (m, 3H).

BIOLOGICAL ACTIVITY EXAMPLES

For all of the biological activity examples that follow, Compound CR was produced in accordance with chemical synthesis example 1.

Example 2

Antidiabetic Effects of Compound CR in db/db mice—4 Weeks

Db/db mice have a defect in leptin signaling, leading to hyperphagia, obesity and diabetes. Moreover, unlike ob/ob mice on a C57BL/6J background, db/db mice on a C57BLKS background undergo failure of their insulin-producing pancreatic islet cells, resulting in progression from hyperinsulinemia (associated with peripheral insulin resistance) to hypoinsulinemic diabetes.

Male obese (db/db homozygote) C57BL/Ksola mice approximately 8 weeks of age, were obtained from Jackson Labs (Bar Harbor, Me.) and randomly assigned into groups of 5-7 animals such that the body weights (40-45 g) and serum glucose levels ($\geq$300 mg/dl in fed state) were similar between groups; male lean (db/+heterozygote) mice served as cohort controls. A minimum of 7 days was allowed for adaptation after arrival. All animals were maintained under controlled temperature (23° C.), relative humidity (50±5%) and light (7:00-19:00), and allowed free access to standard chow (Formulab Diet 5008, Quality Lab Products, Elkridge, Md.) and water.

Treatment cohorts were given daily oral doses of vehicle, Compound BI (100 mg/kg), or Compound CR (100 mg/kg) for 4 weeks. At the end of the treatment period 100 µl of venous blood was withdrawn in a heparinized capillary tube from the retro-orbital sinus for serum chemistry analysis.

After 4 weeks of daily oral dosing, both Compound BI and Compound CR elicited a significant reduction in blood glucose (Table I). Both compounds also reduced serum triglycerides and free fatty acids (Table II) versus vehicle-treated db/db mice.

TABLE I

Effect of Compounds BI and CR on serum glucose in b/db mice: Treatment for 4 weeks

| Groups | Glucose ± SEM mg/dL |
|---|---|
| Lean Control | 193 ± 11 |
| Vehicle (db/db) | 747 ± 19 |
| Cpd. BI - 100 mg/kg | 189 ± 25* |
| Cpd. CR - 100 mg/kg | 235 ± 49* |

*p < 0.05 significantly lower than in vehicle-treated mice

TABLE II

Effect of Compounds BI and CR on serum triglycerides and
free fatty acids in db/db mice: Treatment for 4 weeks

| Group | Triglycerides ± SEM mg/dL | Free Fatty Acids ± SEM μM |
|---|---|---|
| Lean | 96.4 ± 6.4 | 1637 ± 105 |
| Vehicle | 621 ± 54 | 2415 ± 134 |
| Cpd. BI | 125 ± 11* | 1387 ± 101* |
| Cpd. CR | 182 ± 29* | 1634 ± 78* |

*= p < .05 significantly lower than vehicle-treated values

Example 3

Antidiabetic Effects of Compound CR in db/db Mice—2 Weeks

The same procedure as Example 2 was followed. After 2 weeks of daily oral dosing, both Compound BI and Compound CR elicited a significant reduction in blood glucose (Table III).

Both compounds markedly reduce triglycerides; however at 2 weeks BI and not CR caused a decrease in free fatty acids (Table IV) as described below. (Compound CR did result in a decrease in free fatty acids at 4 weeks as described above in Example 2.)

TABLE III

The effects of Compounds BI and CR in
a db/db mouse model of type I diabetes

| Groups | Glucose mg/dL | Glucose (% of Control) |
|---|---|---|
| Vehicle (Control) | 752.9 ± 46.0 | 100 ± 6 |
| BI - 100 mg/kg | 317.4 ± 48.0* | 42 ± 6* |
| CR - 100 mg/kg | 263.2 ± 59.0* | 35 ± 8 |

*p < 0.05 significantly different compared with vehicle-control

TABLE IV

Effect of Compounds BI and CR on plasma serum glucose,
triglycerides, and free fatty acids in db/db mice

| Group | Glucose ± SEM | Triglycerides ± SEM | Free Fatty Acids ± SEM |
|---|---|---|---|
| Lean | 212.6 ± 15.3 | 96.4 ± 6.4 | 1417.2 ± 54.3 |
| Vehicle | 752.9 ± 46.0 | 388.0 ± 50.7 | 1245.9 ± 71.5 |
| BI | 317.4 ± 48.0 | 136.3 ± 18.1 | 1070.3 ± 96.4 |
| CR | 263.2 ± 59.0 | 86.3 ± 9.4 | 1326.3 ± 124.2 |

What is claimed is:

1. A biologically active agent, wherein the agent is a compound of the formula:

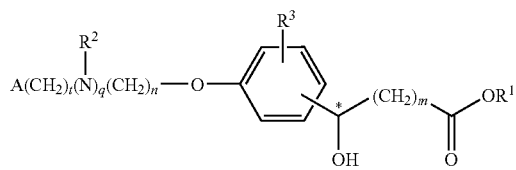

Formula I wherein n is 1 or 2;
m is 0, 1, 2, 3 or 4;
q is 0 or 1;
t is 0 or 1;
$R^2$ is alkyl having from 1 to 3 carbon atoms;
$R^3$ is hydrogen, halo, alkyl having from 1 to 3 carbon atoms, or alkoxy having from 1 to 3 carbon atoms;
A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy; or
  cycloalkyl having from 3 to 6 ring carbon atoms wherein the cycloalkyl is unsubstituted or one or two ring carbons are independently mono-substituted by methyl or ethyl; or
  a 5 or 6 membered heteroaromatic ring having 1 or 2 ring heteroatoms selected from N, S and O and the heteroaromatic ring is covalently bound to the remainder of the compound of formula I by a ring carbon; and
$R^1$ is hydrogen or alkyl having 1 or 2 carbon atoms, provided that when m is 0 or 1, $R^1$ is not hydrogen;
or when $R^1$ is hydrogen, a pharmaceutically acceptable salt of the compound, wherein the agent is substantilly pure.

2. The biologically active agent of claim 1, wherein n is 1; q is 0; t is 0; $R^3$ is hydrogen; and
A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy.

3. The biologically active agent of claim 2, wherein wherein A is 2,6-dimethylphenyl.

4. The biologically active agent of claim 3, 4-(3-(2,6-Dimethylbenzyloxy)-phenyl)-4-hydroxybutanoic acid.

5. A biologically active agent, wherein the agent is a compound of the formula:

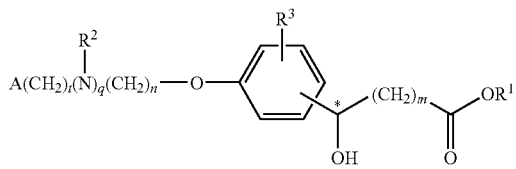

Formula I wherein n is 1 or2;
m is 0,1,2,3 or 4;
q is 0 or 1;
t is 0 or 1;
$R^2$ is alkyl having from 1 to 3 carbon atoms;
$R^3$ is hydrogen, halo, alkyl having from 1 to 3 carbon atoms, or alkoxy having from 1 to 3 carbon atoms;
A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy; or
  cycloalkyl having from 3 to 6 ring carbon atoms wherein the cycloalkyl is unsubstituted or one or two ring carbons are independently mono-substituted by methyl or ethyl; or
  a 5 or 6 membered heteroaromatic ring having 1 or 2 ring heteroatoms selected from N, S and 0 and the heteroaromatic ring is covalently bound to the remainder of the compound of formula I by a ring carbon; and
$R^1$ is hydrogen or alkyl having 1 or 2 carbon atoms, provided that when m is 0 or 1, $R^1$ is not hydrogen;

or when R¹ is hydrogen, a pharmaceutically acceptable salt of the compound, wherein the agent is present in a mammal other than a mouse.

6. The biologically active agent of claim 5, wherein n is 1; q is 0; t is 0; R³ is hydrogen; and
A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy.

7. The biologically active agent of claim 6, wherein A is 2,6-dimethylphenyl.

8. The biologically active agent of claim 7, 4-(3-(2,6-Dimethylbenzyloxy)-phenyl)-4-hydroxybutanoic acid.

9. The biologically active agent of claim 8, wherein the mammal is a human.

10. The biologically active agent of claim 5, wherein the mammal is a human.

11. A pharmaceutical composition comprising a pharmaceutically acceptable carrier and from one milligram to four hundred milligrams of a biologically active agent, wherein the agent is a compound of the formula:

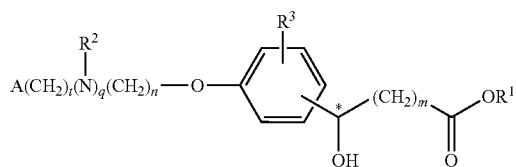

Formula I wherein
n is 1 or 2;
m is 0,1,2,3 or 4;
q is 0 or 1;
t is 0 or 1;
R² is alkyl having from 1 to 3 carbon atoms;
R³ is hydrogen, halo, alkyl having from 1 to 3 carbon atoms, or alkoxy having from 1 to 3 carbon atoms;
A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy; or
cycloalkyl having from 3 to 6 ring carbon atoms wherein the cycloalkyl is unsubstituted or one or two ring carbons are independently mono-substituted by methyl or ethyl; or
a 5 or 6 membered heteroaromatic ring having 1 or 2 ring heteroatoms selected from N, S and O and the heteroaromatic ring is covalently bound to the remainder of the compound of formula I by a ring carbon; and
R¹ is hydrogen or alkyl having 1 or 2 carbon atoms, provided that when m is 0 or 1, R¹ is not hydrogen;
or when R¹ is hydrogen, a pharmaceutically acceptable salt of the compound.

12. The pharmaceutical composition of claim 11, wherein n is 1; q is 0; t is 0;R³ is hydrogen; and
A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy.

13. The pharmaceutical composition of claim 12, wherein A is 2,6-dimethylphenyl.

14. The pharmaceutical composition of claim 13, wherein the biologically active agent is 4-(3-(2,6-Dimethylbenzyloxy)-phenyl)-4-hydroxybutanoic acid.

15. The pharmaceutical composition of claim 11 in oral dosage form.

16. A method for treating a mammalian subject with a condition selected from the group consisting of insulin resistance syndrome,and Type II Diabetes, comprising administering to the subject an amount of a biologically active agent, wherein the agent is a compound of the formula:

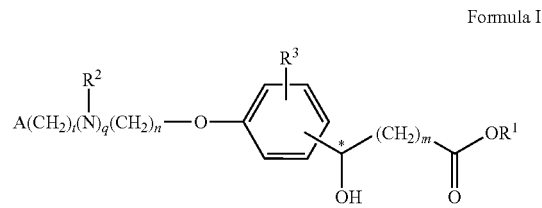

Formula I wherein
n is 1 or 2;
m is 0, 1, 2, 3 or 4;
q is 0 or 1;
t is 0 or 1;
R² is alkyl having from 1 to 3 carbon atoms;
R³ is hydrogen, halo, alkyl having from 1 to 3 carbon atoms, or alkoxy having from 1 to 3 carbon atoms;
A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy; or
cycloalkyl having from 3 to 6 ring carbon atoms wherein the cycloalkyl is unsubstituted or one or two ring carbons are independently mono-substituted by methyl or ethyl; or
a 5 or 6 membered heteroaromatic ring having 1 or 2 ring heteroatoms selected from N, S and O and the heteroaromatic ring is covalently bound to the remainder of the compound of formula I by a ring carbon; and
R¹ is hydrogen or alkyl having 1 or 2 carbon atoms, provided that when m is 0 or 1, R¹ is not hydrogen;
or when R¹ is hydrogen, a pharmaceutically acceptable salt of the compound.

17. The method of claim 16, wherein n is 1; q is 0; t is 0; R³ is hydrogen; and
A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy.

18. The method of claim 17, wherein A is 2,6-dimethylphenyl.

19. The method of claim 18, wherein the biologically active agent is 4-(3-(2,6-Dimethylbenzyloxy)-phenyl)-4-hydroxybutanoic acid.

20. The method of any one of claims 16 to 19, wherein the subject is a human.

21. The method of claim 20, wherein the agent is administered orally in an amount from one milligram to four hundred milligrams per day.

22. The method of claim 16, wherein the treatment reduces a symptom of diabetes or the chances of developing a symptom of diabetes, wherein the symptom is selected from the group consisting of: atherosclerosis, obesity, hypertension, hyperlipidemia, fatty liver disease, nephropathy, neuropathy, retinopathy, foot ulceration and cataracts, associated with diabetes.

* * * * *

UNITED STATES PATENT AND TRADEMARK OFFICE
CERTIFICATE OF CORRECTION

| | | |
|---|---|---|
| PATENT NO. | : 7,514,555 B2 | Page 1 of 1 |
| APPLICATION NO. | : 10/531618 | |
| DATED | : April 7, 2009 | |
| INVENTOR(S) | : Hodge et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 241 days.

Signed and Sealed this
Twenty-third Day of August, 2011

David J. Kappos
*Director of the United States Patent and Trademark Office*